United States Patent [19]

Hessel et al.

[11] Patent Number: 5,298,025
[45] Date of Patent: Mar. 29, 1994

[54] SEQUENTIAL FLOW RATE INFUSION RATE

[75] Inventors: Steve Hessel, Fountain Valley; William C. Brown, Huntington Beach, both of Calif.

[73] Assignee: Baxter International Inc., Deerfield, Ill.

[21] Appl. No.: 46,516

[22] Filed: Apr. 12, 1993

Related U.S. Application Data

[63] Continuation of Ser. No. 726,475, Jul. 8, 1991, abandoned.

[51] Int. Cl.⁵ .................. A61M 11/00; A61M 1/00; A61M 37/00
[52] U.S. Cl. ..................... 604/93; 604/118; 604/132; 128/DIG. 12
[58] Field of Search ............ 604/51–53, 604/82, 83, 85, 89, 90, 93, 118, 131, 132, 153, 183, 246, 256, 891.1; 128/DIG. 12

[56] References Cited

U.S. PATENT DOCUMENTS

| | | | |
|---|---|---|---|
| 2,589,728 | 3/1952 | Pratt | 604/131 X |
| 3,698,595 | 10/1972 | Gortz et al. | |
| 3,767,078 | 10/1973 | Gortz et al. | |
| 4,391,600 | 7/1983 | Archibald | 604/153 |
| 4,544,371 | 10/1985 | Dormandy, Jr. et al. | 604/891 |
| 4,548,607 | 10/1985 | Harris | 604/891.1 |
| 4,702,397 | 10/1987 | Gortz | |
| 4,741,733 | 5/1988 | Winchell et al. | 604/51 |
| 4,769,008 | 9/1988 | Hessel | 604/132 |
| 4,857,055 | 8/1989 | Wang | 604/133 |
| 4,915,693 | 4/1990 | Hessel | 604/132 |
| 5,011,477 | 4/1991 | Winchell et al. | |
| 5,019,047 | 5/1991 | Kriesel | 604/132 |
| 5,049,141 | 9/1991 | Olive | 604/891 |
| 5,080,652 | 1/1992 | Sancoff et al. | 604/132 |
| 5,135,497 | 8/1992 | Hessel et al. | 604/132 |

*Primary Examiner*—John D. Yasko
*Assistant Examiner*—Adam J. Cermak
*Attorney, Agent, or Firm*—Paul E. Schaafsma; Amy L. H. Rockwell; Paul C. Flattery

[57] ABSTRACT

The present invention provides a casing having a plurality of sources of pressurized liquid. The sources of pressurized liquid are preferably contained in at least one elastomeric bladder. Housing is provided to establish fluid communication between the sources of pressurized liquid. Additionally, at least one flow restrictor is provided to regulate the flow of pressurized liquid. A single or a plurality of flow restrictors can be used to regulate the flow of liquid between the sources of pressurized liquid. The plurality of sources of pressurized liquid can be contained under different pressures which can be provided by varying the size of the elastomeric storage area. The casing further contains an inlet port and an exit port in fluid communication with the sources of pressurized liquid to provide for filling and dispensing of the fluid.

16 Claims, 5 Drawing Sheets

SEQUENTIAL FLOW RATE INFUSION RATE

This is a continuation of application Ser. No. 07/726,475 filed on Jul. 8, 1991, now abandoned.

FIELD OF THE INVENTION

The present invention relates to the controlled delivery of fluids and, in particular, to portable apparatus for delivery of a medical fluid having a beneficial agent to a patient.

BACKGROUND OF THE INVENTION

Devices for infusing to a patient a beneficial agent such as a drug diffused in a medical liquid are known in the art. The most common device utilizes an elevated glass or flexible container having the beneficial agent diffused in a medical liquid which is fed by gravity to a patient's venous system via a length of flexible plastic tubing and a catheter. The rate of flow in this setup is commonly regulated by an adjustable clamp on the tubing. This setup suffers from the drawback of requiring a relatively stationary patient and is dependent on the height differential between this source of liquid and the patient for accurate delivery rates.

An additional type of infusion device utilizes electro-mechanical components in a pump to provide fluid propulsion of the liquid for infusion into the patient. Such electronically controlled infusion devices, however, suffer from several drawbacks including the cost of such electrical components as well as the limit such electrical components and the necessary power source place on the size and thus portability of the device.

Devices in the art are also utilized which employ an elastomeric bladder which contains the liquid to be infused under pressure for infusion. Such elastomeric bladder infusion devices are seen in U.S. Pat. No. 4,741,733 to Winchell et al. and U.S. Pat. No. 4,769,008 to Hessel, both of which are assigned to the assignee of the present invention.

While such elastomeric bladder infusion devices such as seen in the Hessel and Winchell et al. patents provide an accurate flow of the liquid being infused over an extended period of time, the rate of flow of the liquid being infused is limited to a single flow rate. While electro-mechanical pumping devices can include circuitry to allow programming of a variety of sequential flow rates, such additional electrical components further add to the size and cost of such devices. In the gravity fed type of infusion device, sequential infusion rates are achieved by manually adjusting the adjustable flow clamp.

What would thus be desirable would be an infusion device capable of providing sequential flow rates of the infused liquid which would be portable to allow the patient free movement while providing for sequential flow rates. Additionally, such device should not be cost prohibitive. The present invention meets these requirements.

SUMMARY OF THE INVENTION

The present invention provides a casing having a plurality of sources of pressurized liquid. The sources of pressurized liquid are preferably contained in at least one elastomeric bladder. Housing is provided to establish fluid communication between the sources of pressurized liquid. Additionally, at least one flow restrictor is provided to regulate the flow of pressurized liquid. A single or a plurality of flow restrictors can be used to regulate the flow of liquid between the sources of pressurized liquid. The plurality of sources of pressurized liquid can be contained under different pressures which can be provided by varying the size of the elastomeric storage area. The casing further contains an inlet port and an exit port in fluid communication with the sources of pressurized liquid to provide for filling and dispensing of the fluid.

DETAILED DESCRIPTION OF THE PRESENTLY PREFERRED EMBODIMENT

Figure 1:
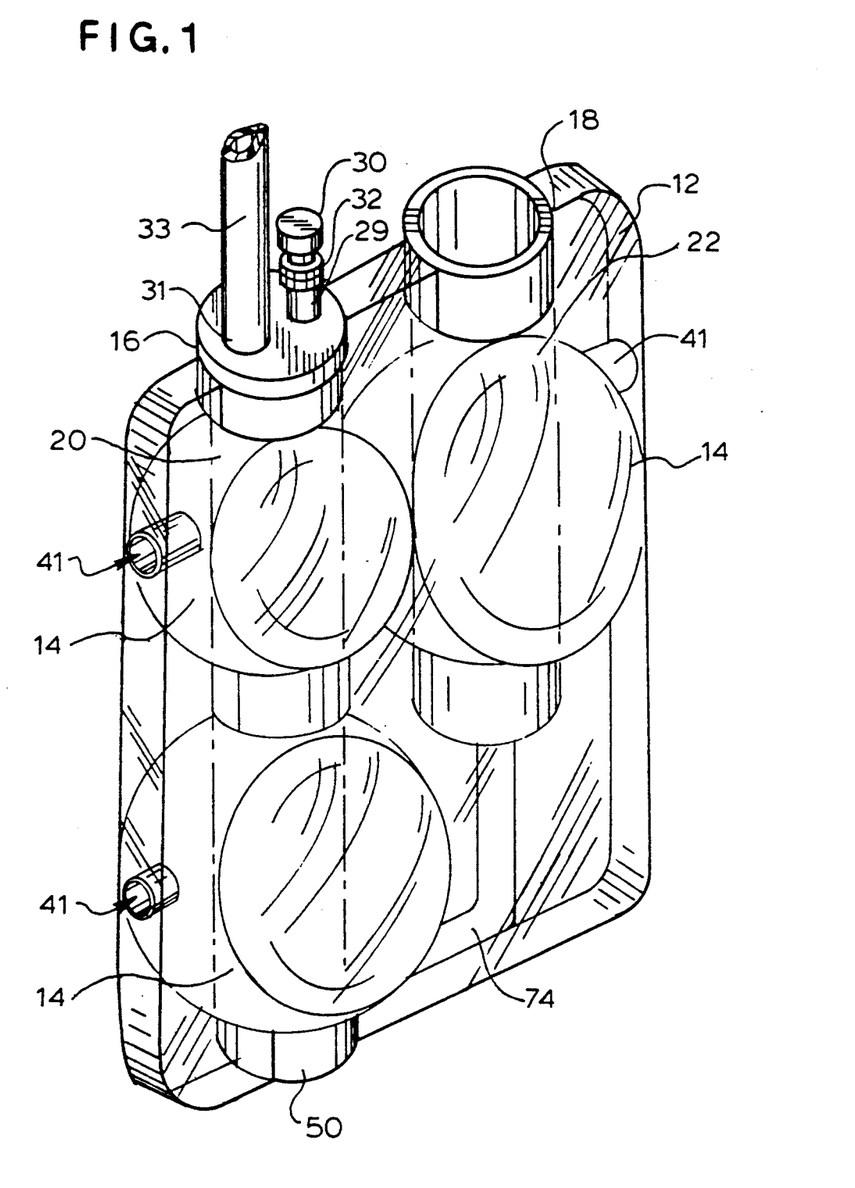
FIG. 1 is a perspective view of an embodiment of an infusion device made in accordance with the principles of the present invention.

Referring to FIG. 1, an infusion device made in accordance with the principles of the present invention is designated generally by the reference numeral 10. The device includes a casing 12 which can be formed from any of a variety of known thermal distortion multiple polymeric materials such as acrylic or styrene, which will protect the bladder from ultra-violet light yet is substantially transparent to visible light to permit visual inspection of the internal components.

Casing 12 includes a plurality of bulb-shaped expanded internal cavities 14 which correspond in number to the number of sources of pressurized fluid contained in the device 10. In the embodiment depicted herein, three sources of pressurized liquid are provided. The casing 12 is provided having a pair of openings 16,18 at the proximal end. The openings 16,18 are adapted for receiving corresponding prestress members 20,22. Contained within the casing 12 and aligned with the internal cavities 14 are a pair of elastomeric bladders 24,26 as will be described in more detail below.

The first prestress member 20 includes a fill port 29 and an exit port 31 at the proximal end thereof. The fill port 29 can preferably be provided with a female luer for connection to a filling apparatus. A double luer cap 32 can be provided which has a male luer for engagement with the female luer on the fill port 29 and a female luer for engagement with a male luer cap 30. When the male luer cap 30 is removed for filling the bladders 24,26, the double luer cap 32 remains aseptic and may be detached from the female luer of the fill port 29 for sealing the fill port 29. Alternatively, the double luer may be aseptically sealed with a sealing membrane. The sealing membrane may be removed at the time of filling and, after filling, the filling port may be sealed with the male luer cap 30.

Sealingly attached to the exit port 31 is conventional I.V. tubing 33. The tubing 33 is secured at its proximal end to a tubing seat 35 provided in the exit port 31. The distal end of the tubing 33 is connected to a rigid plastic housing 37 by adhesive or the like. The rigid plastic housing 37 can preferably include a luer connector for connection to a catheter to be inserted into the patient's venous system. In a first preferred embodiment, the rigid plastic housing 37 can also include a flow regulator such as a glass capillary flow regulator as seen and described in U.S. Pat. No. 4,741,733 entitled "INFUSOR HAVING A DISTAL FLOW REGULATOR", the disclosure of which is incorporated herein by this reference. Finally, a conventional tubing clamp 39 can be provided on the tubing 33 which will be normally clamped during catheterization.

Figure 2:
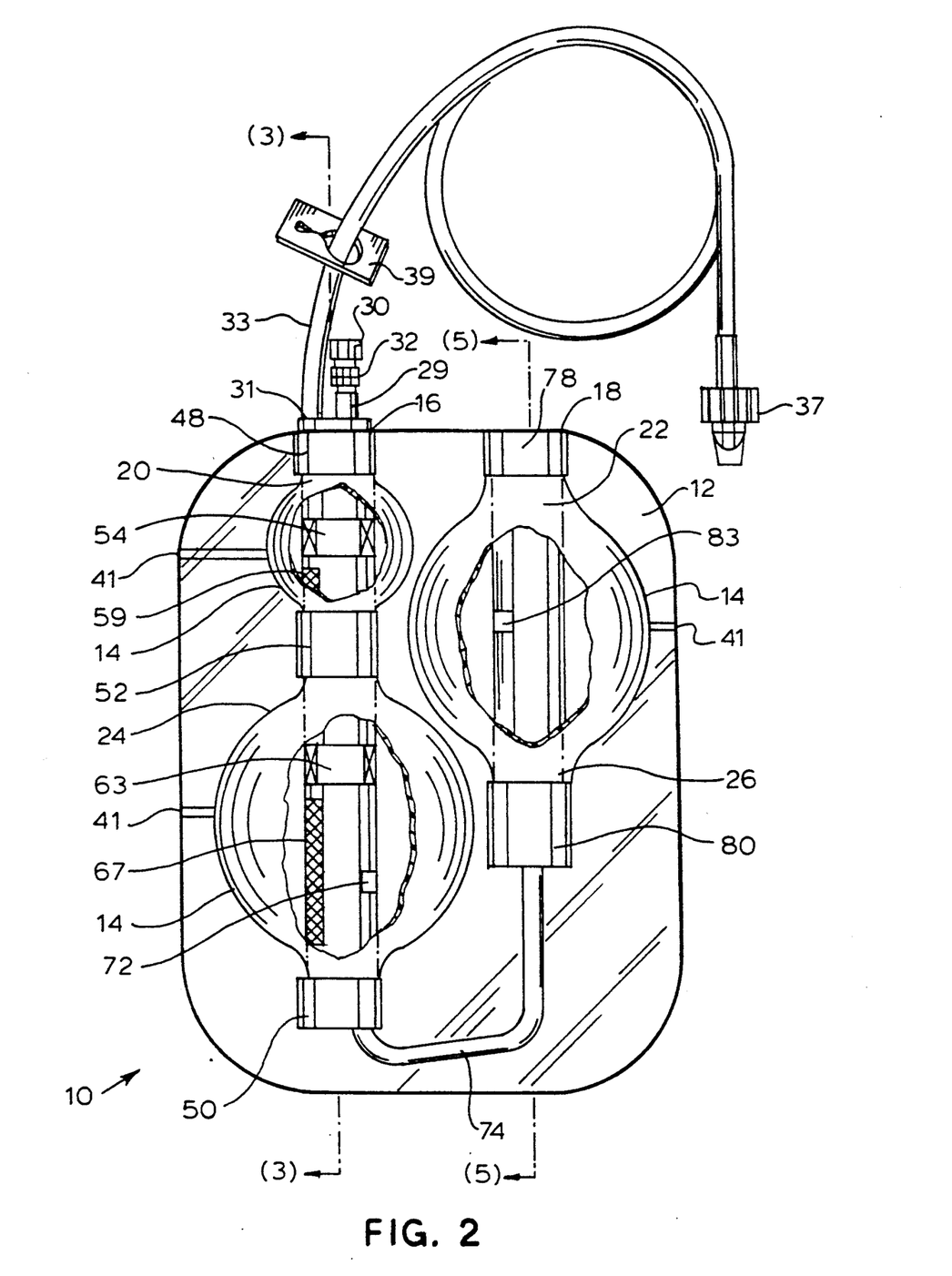
FIG. 2 is an elevational schematic view of the device of FIG. 1 shown with the elongated elastomeric bladder in its filled state.

Referring now to FIG. 2, a cut-away schematic view of the present device is seen. The internal cavities 14 define an upper limit on the size of the sources of pressurized liquid. Additionally, the internal cavities 14 define the location of the sources of pressurized liquid. Air vents 41 are provided for each internal cavity 14 to enable air to escape during filling.

The pair of prestress members 20,22 are contained in proximal openings in the casing 12. The prestress members 20,22 can be produced in accordance with known thermoplastic forming techniques and can preferably comprise acrylic, styrene, or any other rigid thermoplastic material that is substantially inert in the environment of the intended pharmaceutically active material. If it is desirable from a manufacturing standpoint, the prestress members 20,22 may be formed from other materials and thereafter provided with a continuous coating of an appropriate inert substance. The prestress members 20,22 preferably have a substantially uniform, circular cross-sectional shape throughout the actual length.

The first prestress member 20 has the first elastomeric bladder 24 contained thereon. The first elastomeric bladder 24 includes an open distal end 44 and an open proximal end 46 (best seen in FIG. 6). The first elastomeric bladder 24 includes an elastic, generally cylindrical member which defines an interior space, which, in the unexpanded state, is of known interior cross-sectional and axial dimensions. The diameter of the first prestress member 20 is thus provided slightly larger than the known internal diameter of the first elastomeric bladder 24.

The first elastomeric bladder 24 is coaxially disposed around and in engagement with the first prestress member 20. The open proximal end 46 and distal end 44 are secured to the first prestress member 20 in a sealing engagement by means such as a proximal annular clamp 48 and a distal annular clamp 50 extending therearound. Additionally, to provide for two separate pressurized sources of liquid within the first elastomeric bladder 24, a medial annular clamp 52 is disposed around the first elastomeric bladder 24 and the first prestress member 20 between the proximal end 46 and distal end 44.

The first prestress member 20 further includes an elastic valve band 54 disposed coaxially about the first prestress member 20 between the proximal annular clamp 48 and the medial annular clamp 52. The first prestress member 20 is preferably provided with an annular recess for receiving the valve band 54 so that the outside diameter of the valve band 54 is substantially the same as the diameter of the adjacent portions of the first prestress member 20.

Contained under the valve band 54 is a transverse influent duct 56 which is in fluid communication with the filling port 29. The valve band 54 acts as a one-way valve to allow flow of fluid into the first pressurized fluid storage area while preventing back flow out the transverse influent duct 56.

Further contained on the first prestress member 20 is a screen or mesh 59 welded in place between the proximal annular clamp 48 and the medial annular clamp 52. A shallow depression can again be provided on the first prestress member 20 for receiving the screen or mesh 59 such that the outside diameter of the screen 59 is substantially the same as the diameter of the adjacent portions of the first prestress member 20. Contained under the screen or mesh 59 is an effluent duct 61 which is in fluid communication with the exit port 31. The screen or mesh 59 may be made of stainless steel, platinum wire, or other suitable material or any of a variety of polymers such as polytetrafluoroethylene having a porous or multifilament configuration capable of operating as a screen, and which will be substantially unreactive in the presence of the pharmaceutical material. The porous size of the mesh or screen 59 should be large enough so that the sum of the flow paths through the mesh or screen 59 will permit sufficient flow that the mesh or screen 59 will not be a factor in the overall flow rate of the device.

Further provided on the first prestress member 20 between the distal annular clamp 50 and the medial annular clamp 52 is a second elastic valve band 63 disposed coaxially about the first prestress member 20. Once again, the first prestress member 20 is provided with an annular recess for receiving the valve band 63 so that the outside diameter of the valve band 63 is substantially the same as the diameter of the adjacent portion of the first prestress member 20.

Contained under the second valve band 63 is a second influent duct 65 which is in fluid communication with both the first influent duct 56 and the filling port 29. Again, the second valve band 63 acts as a one-way valve to permit flow into the second source of pressurized fluid while preventing back flow to the filling port 29.

Further provided on the first prestress member 20 between the distal annular clamp 50 and the medial annular clamp 52 is a second screen or mesh 67 held in place by an adhesive. Once again, the first prestress member 20 is provided with a shallow depression for receiving the second screen or mesh 67 such that the outside diameter of the second screen or mesh 67 is substantially the same as the diameter of the adjacent portions of the first prestress member 20. Contained under the second screen or mesh 67 is a second effluent duct 69 which is in fluid communication with the first effluent duct 61 as well as the exit port 31.

The first prestress member 20 further includes an intake port 72 between the distal annular clamp 50 and the medial annular clamp 52. The intake port 72 is in fluid communication with a the second prestress member 22 by means of a short length of standard IV tubing 74 secured by adhesive or the like. Alternatively, tubing 74 can be integrally formed in casing 12.

Coaxially contained on the second prestress member 22 is the second elastomeric bladder 26. Once again, the second elastomeric bladder 26 includes an elastic, generally cylindrical member for defining an interior space which, in the unexpanded state, is of known interior cross-sectional and axial dimensions. The outside diameter of the second prestress member 22 is slightly larger than the known internal diameter of the second elastomeric bladder 26 which is contained thereon. Again, the second elastomeric bladder 26 is preferably provided with open proximal 75 and distal ends 76 which are secured to the second prestress member 22 by annular clamps 78,80.

Provided on the second prestress member 22 is an inlet port 83. The second prestress member inlet port 83 is in fluid communication with formed tubing 74 such that means are provided for fluid communication between the second source of pressurized fluid and the third source of pressurized fluid. When liquid is introduced into the second elastomeric bladder 26 via the inlet port 83 of the second prestress member 22, the second elastomeric bladder 26 expands to form the third source of pressurized liquid.

Figure 3:
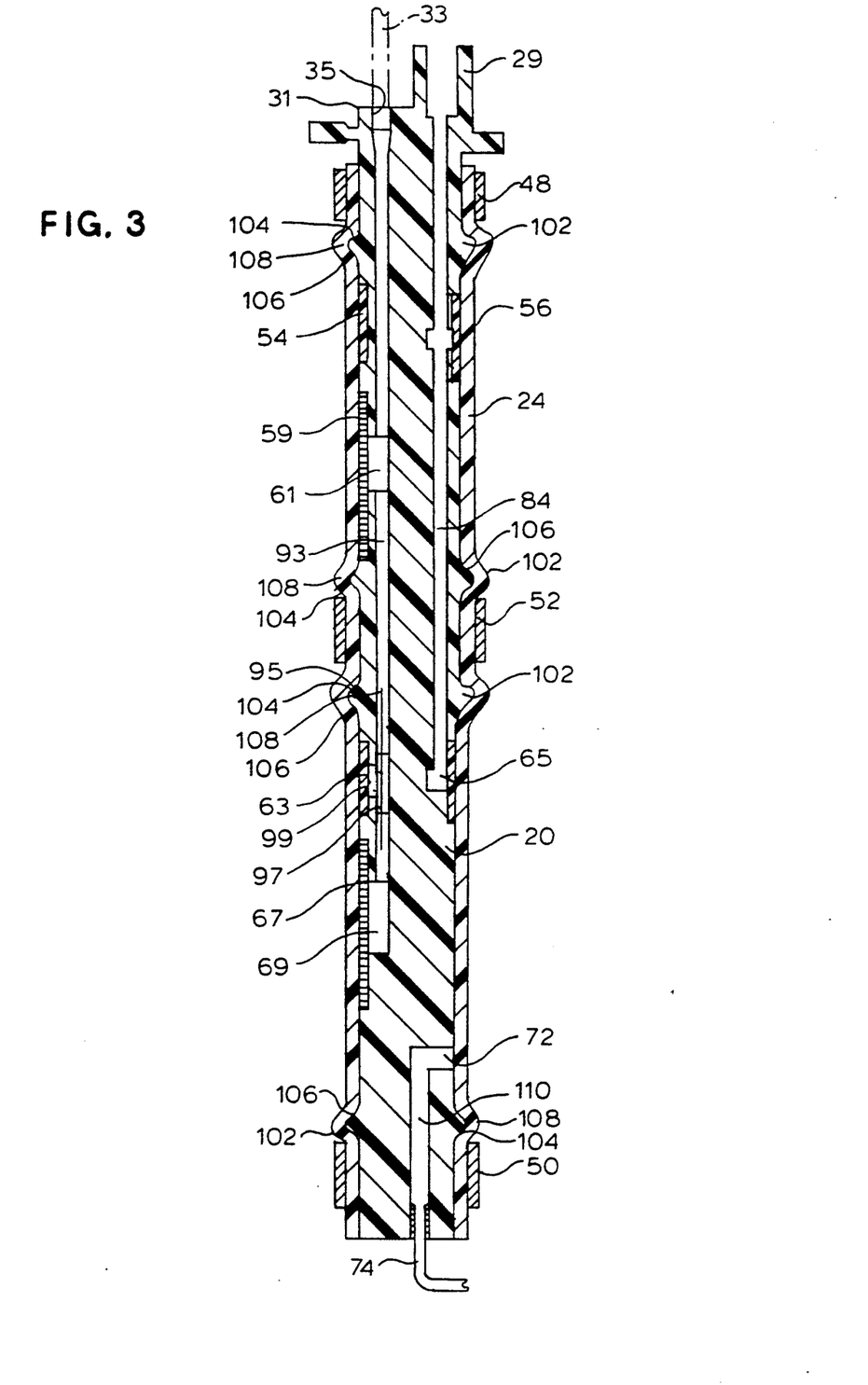
FIG. 3 is an elevational, partial cross-sectional view of the first prestress member of the device of FIG. 1 showing the bladder in the unfilled state.
Figure 4:
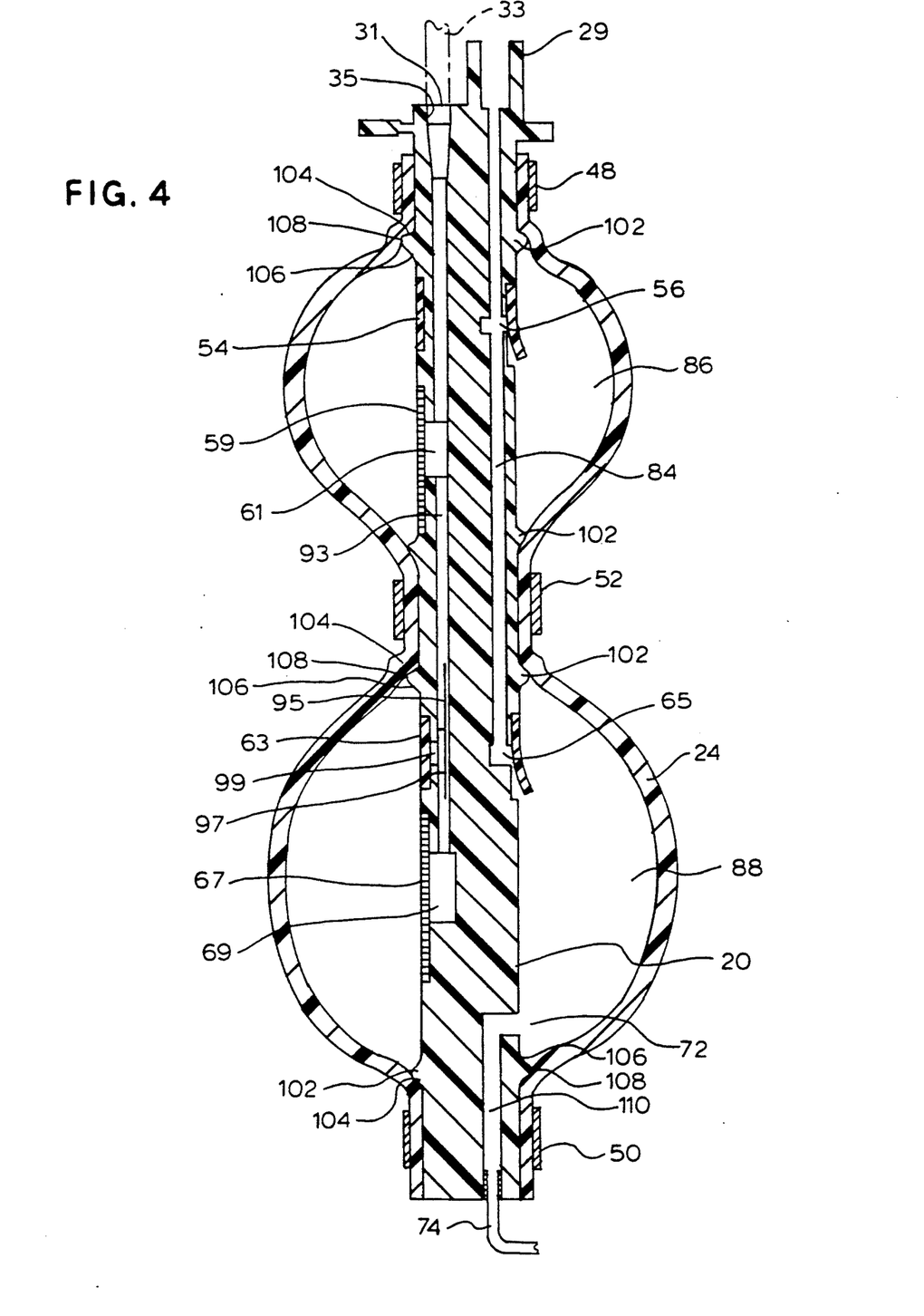
FIG. 4 is an elevational, partial cross-sectional view similar to FIG. 3 showing the elastomeric bladder in its filled state.

Referring now to FIGS. 3 and 4, the first prestress member 20 is seen in detail. Defined in the first prestress member 20 and in fluid communication with the filling port 29, the first influent duct 56, and the second influent duct 65 is an elongated influent lumen 84. To provide liquid from an exterior filling vessel, pressurized liquid is provided at the filling port 29 which is provided at the influent ducts 56,65 via the elongated influent lumen 84. Pressure from an influent stream through the elongated influent lumen 84 will cause momentary displacement of the valve bands 54,63 to permit the influent stream to pass into the interior of the first elastomeric bladder 24 to form the first source of pressurized liquid 86 and the second source of pressurized liquid 88 as seen in FIG. 4. Upon termination of the influent stream, valve bands 54,63 will elastically return to sealingly obstruct the influent ducts 56,65, thereby preventing leakage of material from the interior of the first elastomeric bladder 24 back out through the elongated influent lumen 84. Alternatively, the filling port 29 can include an elastomeric septum capable of being punctured by a sharp cannula and resealable upon withdrawal of the cannula to fill the sources of pressurized liquid.

Also provided in the first prestress member 20 is an elongated effluent lumen 93 in fluid communication with the effluent ducts 61,69 and the exit port 31. Provided in the elongated effluent lumen 93 between the first effluent duct 61 and the second effluent duct 69 is a second flow regulator 95.

The second flow regulator 95 may again comprise a glass capillary tube. The capillary tube can be secured within the elongated effluent lumen 93 by an elastic material or preformed member 97. The adhesive material or preformed member 97 provides sealing engagement between the walls of the elongated effluent lumen 93 and the outside diameter of the second flow regulator 95 to avoid any fluid communication around the outside of the second flow regulator 95.

The first prestress member 20 can be further provided with an access port 99 which allows exposure of the second flow regulator 95 extending through the elongated effluent lumen 93 for receiving a quantity of the adhesive material 97 such as urethane base UV cured epoxy or other material that will be chemically inert in the presence of the pharmaceutically active material contained within the elastomeric bladders. The adhesive material 97 not only secures the second flow regulator 95 but also seals the access port 99. While in the preferred embodiment, the first flow regulator is provided in the rigid plastic housing 37 at the distal end of the I.V. tubiny 33, in an alternative embodiment, this first flow regulator can be similarly inserted in the elongated effluent lumen 93 between the first effluent duct 61 and the exit port 31.

Preferably contained on the first prestress member 20 is a plurality of annular flanges or shoulders 102. The flanges 102 in cooperation with clamps 48,50,52 prevent migration of the first elastomeric bladder 24 in a axial direction due to elastic forces generated by the full elastomeric bladder or by the axial prestressing of the empty elastomeric bladder. The annular flanges 102 comprise a proximal surface 104 and a distal surface 106 which extend radially outwardly from the first prestress member 20 and converge to form a relatively sharp angle at the radially outwardmost portion 108. The distal surface 106 is inclined outwardly from the surface of the first prestress member 20 at a more gradual angle than the proximal surface 104, thereby enhancing the securing function of annular flanges 102. The size of the annular flanges 102 generally is minimized so that it does not factor in the deflation characteristics of the first elastomeric bladder 24. Finally, contained within the distal end of the first prestress member 20 is an auxiliary lumen 110 in fluid communication with the second source of pressurized fluid inlet 72 and the length of internal tubing 74.

Figures 5, 6:
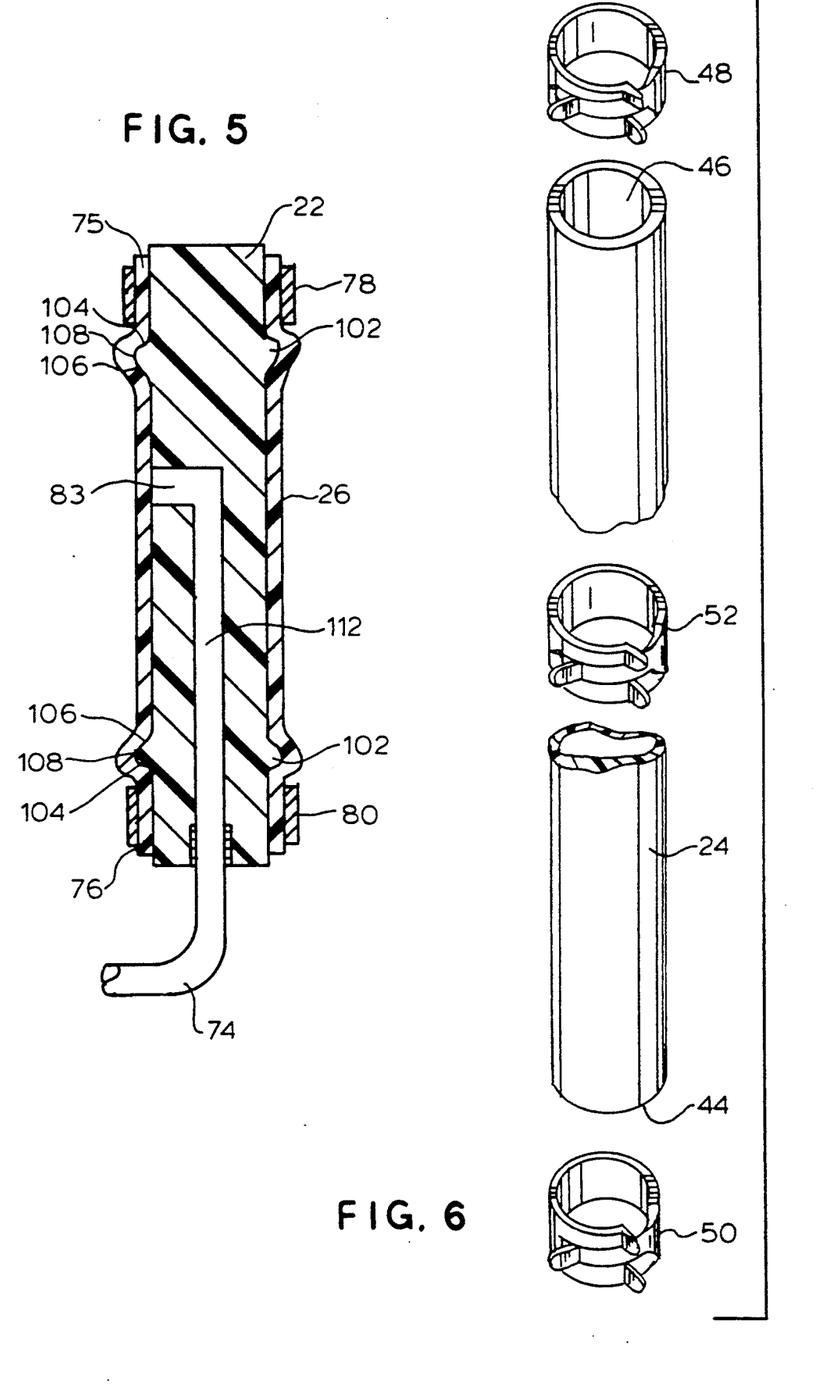
FIG. 5 is an elevational, partially sectional view of the second prestress member of the device of FIG. 1 showing the second bladder in the unfilled state.
FIG. 6 is a perspective view of one embodiment of a bladder of the present invention in an unexpanded state.

Referring now to FIG. 5, an elevated cross-sectional view of the second prestress member 22 is seen. Once again, the inlet port 83 is connected to the internal tubing 74 via an auxiliary lumen 112. A pair of annular flanges or shoulders 102 can again be provided which, in cooperation with distal clamp 80, prevents migration of the second elastomeric bladder 26 in an axial direction due to elastic forces generated by the full elastomeric bladder or by the axial prestressing of the empty elastomeric bladder. Thus, means are provided for fluid communication between the second source of pressurized fluid and the third source of pressurized fluid.

To use, the elastomeric bladders 24,26 are filled by a filling apparatus such as a syringe or pump having a cooperating member such as a luer connector to gain access to the interior of the elastomeric bladders 24,26. The syringe or pump provides liquid containing the beneficial agent at a sufficient pressure to push aside the valve bands 54,63 and fill the elastomeric bladders 24,26 to form the plurality of sources of pressurized liquid.

Because of the prestressing of the elastomeric bladders 24,26, filling expands the elastomeric bladder 24,26 radially while the axial length remains essentially unchanged. Additionally, because of the defined internal cavities 14 corresponding to the sources of pressurized liquid, an upper volume limit of each source of pressurized liquid is defined.

After all the sources of pressurized liquid are full with the expanded elastomeric bladders 24,26 pushing against the internal cavities 14, the syringe or pump is removed. Upon release of the pressure from the filling apparatus, the resilient properties of the valve bands 54,63 act in cooperation with the fluid pressure in the first and second sources of pressurized fluid to close the influent ducts 56,65. This prevents escape of the liquid in the elastomeric bladders 24,26 via the filling port 29.

The tubing 33 is then allowed to prime to eliminate any air contained in the system. The tubing 33 is placed in fluid communication with the patient's venous system via a catheter.

Each of the three sources of pressurized liquid can be adjusted in size and resiliency to provide for different pressurized sources of liquid. Additionally, flow restrictors can be provided in varying degrees of flow restriction. Thus, the different pressurized sources and flow restriction act as means for providing different fluid flow rates from the pressurized sources of liquid.

For example, the first source of pressurized liquid can have the highest pressurization while the first flow restrictor is less restrictive than the second flow restrictor. Likewise, each of the flow restrictors can be varied to provide for different regulation of flow rates from the different sources of pressurized fluid. As will be appreciated by those skilled in the art, different combinations of flow restrictors and degree of pressurized liquid can be utilized to provide multiple combinations of flow rates.

Thus, when infusion starts, the pressurized liquid contained in the first source of pressurized liquid is initially provided to the patient at a relatively high rate of flow. The first flow restrictor, being contained either in the rigid housing 37 at the distal end of the exterior tubing 33 or between the exit port 31 and the first effluent duct 61, regulates the flow rate of this initial bolus delivery.

After the first source of pressurized liquid has delivered its liquid, liquid from the source of pressurized liquid having the next highest pressure is delivered. Continuing the example, the third source of pressurized liquid contains a pressurized source of liquid which is provided via the internal tube 74 to the second source of pressurized liquid. If the pressure being provided from the third source of pressurized liquid is higher than the pressure from the second source of pressurized liquid, the second source of pressurized liquid merely acts as a conduit to forward the liquid from the third source of pressurized liquid. Thus, the fluid in the third source enters via internal tube 74 into the second source of pressurized fluid and then enters through the second effluent duct 69 into the elongated effluent lumen 93.

When placed between the first source of pressurized fluid and the second source of pressurized fluid, the second flow restrictor 95 regulates the flow rates of both the second source of pressurized liquid and the third source of pressurized liquid. In the example, because the second flow restrictor 95 is more restrictive than the first flow restrictor, after delivery of the first source of pressurized fluid, the first flow restrictor passes the liquid from the second and third sources of pressurized liquid to the patient. Thus, while liquid from the third source of pressurized liquid is delivered, a constant flow rate below that of the initial bolus flow rate is provided.

When the third source of pressurized liquid is empty, the liquid from the second source of pressurized liquid takes over. While the second source of pressurized liquid also utilizes the second flow restrictor 95, if the pressure in the second pressurized source is lower than that of the third pressurized source, a lower flow rate is provided.

Thus, by utilizing the present invention, a sequential delivery of beneficial agent comprising first, second and third flow rates can be provided. An example of use of the present invention can be for TPA in which a bolus flow rate, a lysis flow rate, and a maintenance flow rate can be provided. Due to the axial prestressing of the elastomeric bladders, a pressure profile generated by the deflection of each of the sources of pressurized fluid will be substantially constant over each of the sequential flow rates. Additionally, the prestressing of the elastomeric bladder ensures that no air is disposed within the deflated bladders. The only air in the system will be contained in the lumens and I.V. tubing. The prestressing further means that only a minimal amount of the liquid having the beneficial agent will remain in the device after infusion.

It should be understood that various changes and modifications to the preferred embodiment described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A device for infusing liquid into a patient comprising:
   casing defining a plurality of cavities;
   resilient elastomeric bladders corresponding to each of the defined cavities, the elastomeric bladders and the defined cavities defining fluid chambers within the interior of the bladders;
   elongated prestress member contained within the fluid chamber of at least one elastomeric bladder, the prestress member having a substantially uniform, circular cross-sectional shape;
   the casing further defining fluid communication means adapted for providing fluid communication between the plurality of elastomeric bladders to provide a fluid system; and
   housing defining a fill port and an exit port in fluid communication with the plurality of elastomeric bladders.

2. The device of claim 1 wherein the fluid communication means includes lumens defined in the prestress member.

3. The device of claim 1 wherein the fluid chambers include means for providing different fluid flow rates from each of the plurality of fluid chambers.

4. The device of claim 3 wherein the means for providing different fluid flow rates includes providing different sized elastomeric bladders.

5. The device of claim 3 wherein the means for providing different fluid flow rates includes providing at lest one flow restrictor in the fluid system.

6. The device of claim 1 wherein the plurality of elastomeric bladders are in series fluid communication.

7. A device for infusing liquid into a patient comprising:
   casing defining of sources of pressurized liquid in fluid communication with each other to provide a fluid system;
   housing defining a fill port and an exit port in fluid communication with the sources of pressurized liquid; and
   means for providing different fluid flow rates from each of the plurality of sources of pressurized liquid, the means for providing different fluid flow rates comprising at least one capillary tube flow restrictor secured within a lumen in the fluid system.

8. The device of claim 7 wherein the sources of pressurized liquid includes a resilient elastomeric bladder which defines a fluid chamber containing pressurized liquid within the interior of the bladder.

9. The device of claim 8 further wherein the fluid chambers are contained in cavities defined in the casing.

10. The device of claim 8 wherein the means for providing different fluid flow rates further includes providing different sized elastomeric bladders.

11. The device of claim 7 wherein the plurality of sources of pressurized liquid are in series fluid communication with each other.

12. A device for infusing liquid into a patient comprising:

casing defining a plurality of cavities;

resilient elastomeric bladders corresponding to each of the defined cavities, the elastomeric bladders and the defined cavities defining fluid chambers within the interior of the bladders;

a prestress member contained within the fluid chamber of at least one elastomeric bladder;

the casing further defining fluid communication means adapted for providing fluid communication in series between the plurality of elastomeric bladders to provide a fluid system wherein the fluid communication means comprises lumens defined in the prestress member; and housing defining a fill port and an exit port in fluid communication with the plurality of elastomeric bladders.

13. A device for infusing fluid into a patient comprising:

casing defines a plurality of sources of pressurized liquid in fluid communication with each other to provide a fluid system, the sources of pressurized liquid each comprising a resilient elastomeric bladder which defines a fluid chamber for containing pressurized liquid within the interior of the bladder;

housing defining a fill port and an exit portion fluid communication with the sources of pressurized liquid; and means for providing different fluid flow rates from each of the plurality of sources of pressurized liquid, the means for providing different fluid flow rates comprising different sized elastomeric bladders.

14. The device of claim 13 further wherein the fluid cambers are contained in cavities defined in the casing.

15. The device of claim 13 wherein the means for providing different fluid flow rates further includes providing at lest one flow restrictor in the fluid system.

16. The device of claim 13 wherein the plurality of sources of pressurized liquid are in series fluid communication with each other.

* * * * *